United States Patent
Lee et al.

(10) Patent No.: US 10,092,222 B2
(45) Date of Patent: Oct. 9, 2018

(54) METHOD AND APPARATUS FOR USER AUTHENTICATION USING RAMAN SPECTRUM

(71) Applicant: SAMSUNG ELECTRONICS CO., LTD., Suwon-si (KR)

(72) Inventors: June Young Lee, Seongnam-si (KR); Seong Ho Cho, Gwacheon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 110 days.

(21) Appl. No.: 15/242,728

(22) Filed: Aug. 22, 2016

(65) Prior Publication Data

US 2017/0109598 A1 Apr. 20, 2017

(30) Foreign Application Priority Data

Oct. 14, 2015 (KR) .................. 10-2015-0143715

(51) Int. Cl.
| | |
|---|---|
| *G06K 9/00* | (2006.01) |
| *A61B 5/117* | (2016.01) |
| *G01N 21/65* | (2006.01) |
| *A61B 5/00* | (2006.01) |

(52) U.S. Cl.
CPC .......... *A61B 5/117* (2013.01); *A61B 5/0075* (2013.01); *G01N 21/65* (2013.01); *G06K 9/00885* (2013.01); *A61B 2576/00* (2013.01)

(58) Field of Classification Search
CPC ... A61B 5/117; A61B 5/0075; A61B 2576/00; A61B 1/00009; G06K 9/00885; G06K 9/00006; G06K 9/00154; G06K 9/00335; G01N 21/65

USPC ....... 382/100, 115, 128, 132, 168, 181, 190, 382/195, 201, 207; 250/316.1, 459, 1, 250/458.1, 339.11, 341.8; 600/477, 310, 600/316, 476, 322, 335; 340/5.53, 5.83; 427/2.1, 164, 258; 453/6.1; 264/460; 422/69

See application file for complete search history.

(56) References Cited

U.S. PATENT DOCUMENTS

| | | | |
|---|---|---|---|
| 6,205,354 B1 * | 3/2001 | Gellermann | G01N 21/65 356/301 |
| 7,039,446 B2 | 5/2006 | Ruchti et al. | |
| 7,113,814 B2 | 9/2006 | Ward et al. | |
| 7,415,139 B2 * | 8/2008 | Takiguchi | G06K 9/00013 250/341.1 |
| 7,616,123 B2 * | 11/2009 | Ridder | A61B 5/0059 340/573.1 |
| 7,620,212 B1 * | 11/2009 | Allen | G06K 9/0004 340/5.53 |
| 7,751,594 B2 | 7/2010 | Rowe et al. | |
| 7,890,158 B2 | 2/2011 | Rowe et al. | |
| 8,260,402 B2 | 9/2012 | Ermakov et al. | |

(Continued)

FOREIGN PATENT DOCUMENTS

| | | |
|---|---|---|
| JP | 2003331270 A | 11/2003 |
| KR | 100757891 B1 | 9/2007 |

*Primary Examiner* — Sheela C Chawan
(74) *Attorney, Agent, or Firm* — Sughrue Mion, PLLC

(57) ABSTRACT

A user authentication apparatus using a Raman spectrum is provided. The user authentication apparatus includes a Raman spectrum analyzer configured to analyze user characteristic information from a Raman spectrum of a user, and an authenticator configured to authenticate the user, based on the analysis.

16 Claims, 10 Drawing Sheets

(56) References Cited

U.S. PATENT DOCUMENTS

| | | |
|---|---|---|
| 8,811,680 B2 | 8/2014 | Takiguchi |
| 2002/0174346 A1* | 11/2002 | Ting ........................ G06F 21/32 |
| | | 713/186 |
| 2005/0278184 A1 | 12/2005 | Fralick et al. |
| 2011/0275061 A1 | 11/2011 | Weidemaier et al. |

* cited by examiner

METHOD AND APPARATUS FOR USER AUTHENTICATION USING RAMAN SPECTRUM

CROSS-REFERENCE TO RELATED APPLICATION

This application claims priority from Korean Patent Application No. 10-2015-0143715, filed on Oct. 14, 2015, in the Korean Intellectual Property Office, the disclosure of which is incorporated herein by reference in its entirety.

BACKGROUND

1. Field

Methods and apparatuses consistent with exemplary embodiments relate to a method and an apparatus for user authentication, using a Raman spectrum.

2. Description of Related Art

To protect the privacy of an individual user and personal information, biometric authentication technologies have been developed. For example, there are biometric authentication technologies using characteristic information of a unique body for each person such as fingerprint recognition, iris recognition, and the like.

In addition, with the development of portable devices and wearable devices, user personal authentication devices have been diversified, and user personal information that can be obtained from an optical characteristic may include information about the health status of a user, and therefore a healthcare system and user authentication technology are notable areas in the future.

SUMMARY

Exemplary embodiments may address at least the above problems and/or disadvantages and other disadvantages not described above. Also, the exemplary embodiments are not required to overcome the disadvantages described above, and may not overcome any of the problems described above.

Exemplary embodiments provide a method and an apparatus for user authentication, using a Raman spectrum.

According to an aspect of an exemplary embodiment, there is provided a user authentication apparatus using a Raman spectrum, the user authentication apparatus including a Raman spectrum analyzer configured to analyze user characteristic information from a Raman spectrum of a user. The user authentication apparatus further includes an authenticator configured to authenticate the user, based on the analysis.

The Raman spectrum analyzer may be further configured to extract, from the Raman spectrum, data including any one or any combination of a type of the Raman spectrum, a Raman shift of a peak point, and an intensity of the peak point, and analyze the extracted data as the user characteristic information.

The user authentication apparatus may further include a light source configured to irradiate skin of the user with light, and a Raman spectrum acquirer configured to receive light that is reflected from the skin, and acquire the Raman spectrum from the received light.

The light source may be further configured to irradiate the skin of the user with light for a predetermined time, and the Raman spectrum analyzer may be further configured to, in response to fluorescence bleaching occurring in the Raman spectrum over time, extract a fluorescence bleaching range from the Raman spectrum, and analyze the extracted fluorescence bleaching range as the user characteristic information.

The Raman spectrum analyzer may be further configured to extract, from the extracted fluorescence bleaching range, data including either one or both of a principal component composition ratio of the skin of the user and feature information of a first principal component, and analyze the extracted data as the user characteristic information.

The Raman spectrum analyzer may be further configured to extract, from the extracted fluorescence bleaching range, the principal component composition ratio of the skin of the user, using a principal component analysis method.

The feature information of the first principal component may occupy a largest proportion of the principal component composition ratio.

The Raman spectrum analyzer may be further configured to repeatedly measure the feature information of the first principal component at an arbitrary time, and verify reproducibility of the measured feature information of the first principal component.

The user authentication apparatus may further include a storage configured to store the analysis as the user characteristic information, and the authenticator may be further configured to authenticate an identify of the user by comparing the analysis and pre-stored user characteristic information.

The user authentication apparatus may further include an information provider configured to process the analysis with respect to the authenticated user, and provide information of a health status of the authenticated user.

According to an aspect of another exemplary embodiment, there is provided a user authentication method using a Raman spectrum, the user authentication method including analyzing user characteristic information from a Raman spectrum of a user. The user authentication method further includes authenticating the user, based on the analysis.

The analyzing may include extracting, from the Raman spectrum, data including any one or any combination of a type of the Raman spectrum, a Raman shift of a peak point, and an intensity of the peak point, and analyzing the extracted data as the user characteristic information.

The user authentication method may further include irradiating light to skin of the user, receiving light that is reflected from the skin, and acquiring the Raman spectrum from the received light.

The irradiating may include irradiating light to the skin of the user for a predetermined time, and the analyzing may include, in response to fluorescence bleaching occurring in the Raman spectrum over time, extracting a fluorescence bleaching range from the Raman spectrum, and analyzing the extracted fluorescence bleaching range as the user characteristic information.

The analyzing may further include extracting, from the extracted fluorescence bleaching range, data including either one or both of a principal component composition ratio of the skin of the user and feature information of a first principal component, and analyzing the extracted data as the user characteristic information.

The analyzing may further include extracting, from the extracted fluorescence bleaching range, the principal component composition ratio of the skin of the user, using a principal component analysis method.

The feature information of the first principal component may occupy a largest proportion of the principal component composition ratio.

The analyzing may further include repeatedly measuring the feature information of the first principal component at an arbitrary time, and verifying reproducibility of the measured feature information of the first principal component.

The user authentication method may further include storing the analysis as the user characteristic information, and the authenticating may include authenticating an identify of the user by comparing the analysis and pre-stored user characteristic information.

The user authentication method may further include processing the analysis with respect to the authenticated user, and providing information of a health status of the authenticated user.

BRIEF DESCRIPTION OF THE DRAWINGS

The above and/or other aspects will be more apparent by describing exemplary embodiments with reference to the accompanying drawings, in which.

DETAILED DESCRIPTION

Figure 1:
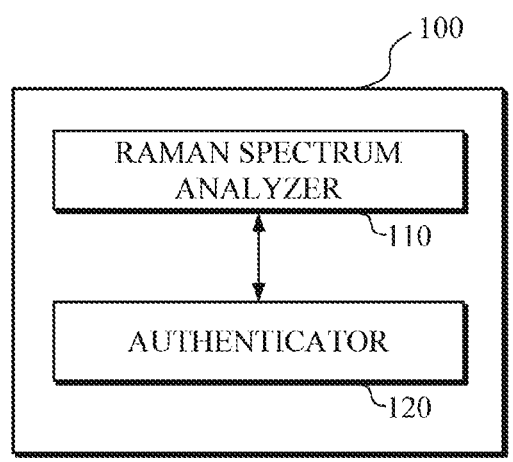
FIG. 1 is a block diagram illustrating a user authentication apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

In addition, the terms such as "unit," "-er (-or)," and "module" described in the specification refer to an element for performing at least one function or operation, and may be implemented in hardware, software, or the combination of hardware and software.

Hereinafter, exemplary embodiments of user authentication apparatuses 100 and 200 and a user authentication method using each of the user authentication apparatuses 100 and 200 will be described in detail with reference to the accompanying drawings. According to an exemplary embodiment, the user authentication apparatuses 100 and 200 using a Raman spectrum may be utilized in portable devices or wearable devices capable of monitoring biomolecules such as healthcare systems, smart phones, smart watches, wrist type bands, and the like.

FIG. 1 is a block diagram illustrating the user authentication apparatus 100 according to an exemplary embodiment. The user authentication apparatus 100 according to an exemplary embodiment of FIG. 1 includes a Raman spectrum analyzer 110 and an authenticator 120.

The Raman spectrum analyzer 110 may analyze a unique characteristic of a user from a Raman spectrum. At this point, as Raman light selectively emits only signals with a wavelength from a narrow wavelength band as inelastic scattering light, it is easy to discern biometric signals as compared to other methods. As an example, a wealth of molecular vibration structure information may be contained in the Raman spectrum, and the information may be used as unique characteristic information for each user. For example, depending on constituent components of a body such as blood sugar, cholesterol, collagen, keratin, etc., and a skin protein component for each user, a different Raman spectrum for each user may be exhibited.

According to an exemplary embodiment, the Raman spectrum analyzer 110 may extract one or more pieces of data from a type of the Raman spectrum, a Raman shift of a peak point, and an intensity of the peak point, and analyze the extracted data as user characteristic information.

Figure 3:
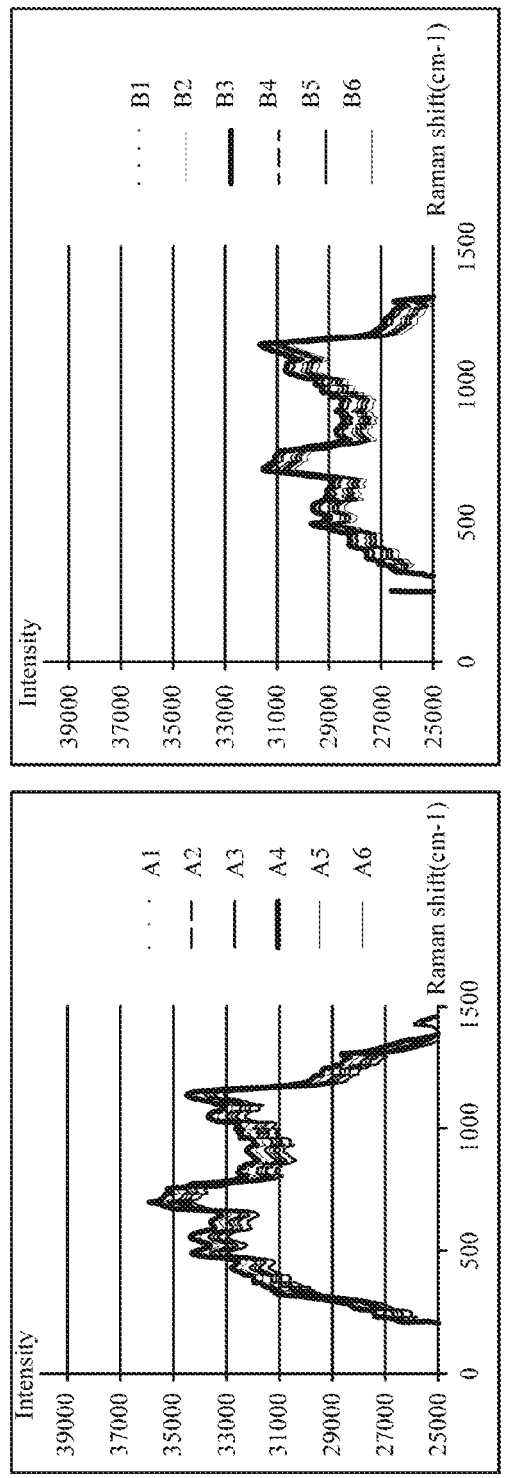
FIG. 3 is a diagram illustrating an example of a Raman spectrum for each user.

FIG. 3 is a diagram illustrating an example of a Raman spectrum for each user. In FIG. 3, an x-axis indicates a Raman shift using a wave number (cm−1) as a unit, and a y-axis indicates the intensity (a.u, arbitrary unit) of a charge-coupled device (CCD) count.

As an example, by measuring the Raman spectrum of a user A six times from A1 to A6, the Raman spectrum may be obtained as shown in view (A) of FIG. 3. Similarly, by measuring the Raman spectrum of a user B six times from B1 to B6, the Raman spectrum may be obtained as shown in view (B) of FIG. 3. The Raman spectrum analyzer 110 may measure the Raman spectrum an arbitrary number of times, select a mean value of the measured Raman spectrum or a representative Raman spectrum, and remove an error that may occur in a measurement process.

According to an exemplary embodiment of FIG. 3, when the Raman spectrum analyzer 110 analyzes the Raman spectrum of the user A, the Raman spectrum of the user A may have a maximum peak point in the vicinity of 700 cm$^{-1}$, and at this point, extract 36,000 a.u as a maximum value of the peak point. In addition, when the Raman spectrum analyzer 110 analyzes the Raman spectrum of the user B, the Raman spectrum of the user B may have a maximum peak point in the vicinity of 700 cm$^{-1}$, and extract 31,500 a.u as a maximum value of the peak point. The Raman spectrum analyzer 110 may analyze data extracted from the Raman spectrum as unique characteristic information for each user.

In addition, the Raman spectrum analyzer 110 may extract peak points, lowest points, the number of the peak points, the number of the lowest points, the intensity of the peak points, variation in the intensity, a mean value of the intensity within a range of a wave number, a deviation from the peak point, and other feature points from each of the Raman spectrums, and analyze the extracted data as the user characteristic information.

Moreover, in an exemplary embodiment, the Raman spectrum analyzer 110 may analyze the user characteristic information using a graph outline analysis method using an image processing technique, a statistical data extraction method, and a quantitative or qualitative analysis method of the Raman spectrum.

The authenticator 120 may authenticate a user based on the analysis result of the Raman spectrum analyzer 110. For example, when the Raman spectrum analyzer 110 analyzes the user characteristic information from the Raman spectrum, the authenticator 120 may determine whether the extracted data coincides with user characteristic information stored in advance based on the analysis result, and authenticate a user's identity using the user authentication apparatus 100.

Figure 2:
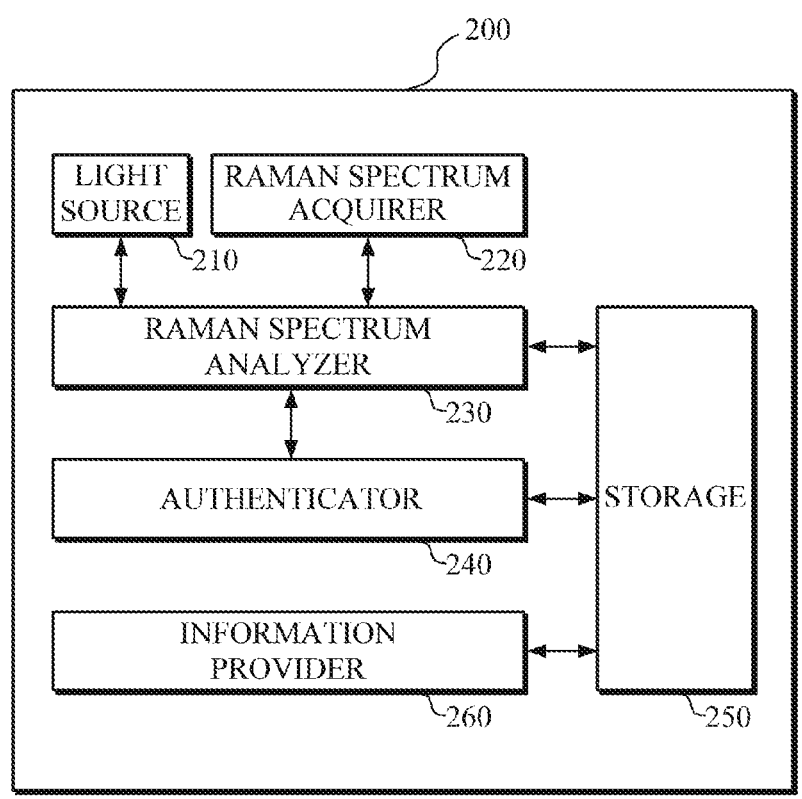
FIG. 2 is a detailed block diagram illustrating a user authentication apparatus according to another exemplary embodiment.

FIG. 2 is a block diagram illustrating the user authentication apparatus 200 according to another exemplary embodiment. Referring to FIG. 2, the user authentication apparatus 200 includes a light source 210, a Raman spectrum acquirer 220, a Raman spectrum analyzer 230, an authenticator 240, a storage 250, and an information provider 260. Hereinafter, description of duplicate components in an exemplary embodiment of FIG. 2 will be simplified.

The light source 210 may irradiate a user's skin with a single light. In this case, the single light may be a short wavelength light such as a laser.

The Raman spectrum acquirer 220 may receive light reflected from the user's skin, and acquire a Raman spectrum from the received light.

As an example, the user authentication apparatus 200 may be mounted or embedded in a hardware device such as a spectrometer including the light source 210 and the Raman spectrum acquirer 220 or a Raman spectroscope. In this case, the spectrometer or the Raman spectroscope may have a shield layer that blocks the inflow of external light except from a skin contact surface to separate light emitted from the light source 210 therein and light emitted from the outside.

In an exemplary embodiment, a device and equipment for acquiring the Raman spectrum is not limited to a specific embodiment, and the user authentication apparatus 200 may be mounted in a portable device, a wearable device, a healthcare system, and the like including the light source 210 and the Raman spectrum acquirer 220.

According to another exemplary embodiment, the light source 210 may irradiate a user's skin with a single light for a predetermined time, and the Raman spectrum acquirer 220 may acquire a Raman spectrum that is exposed for the predetermined time. At this point, when fluorescence bleaching occurs in the Raman spectrum over time, the Raman spectrum analyzer 230 may extract a fluorescence bleaching range and analyze the extracted fluorescence bleaching range as user characteristic information.

Figure 4:
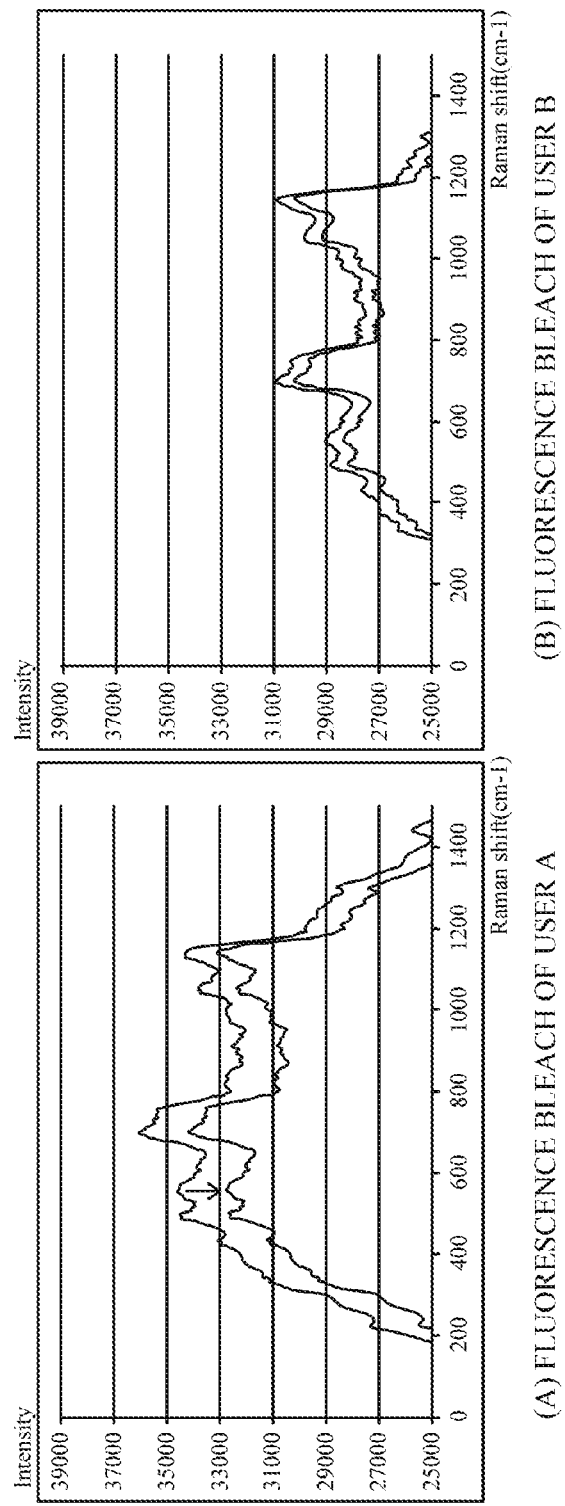
FIG. 4 is a diagram illustrating a range of fluorescence bleaching that occurs after exposure for a predetermined time for each user, according to an exemplary embodiment.

FIG. 4 is a diagram illustrating a range of fluorescence bleaching that occurs after exposure for a predetermined time for each user, according to an exemplary embodiment. When the light source 210 irradiates skin with a single light for the predetermined time, fluorescence may be generated by a protein component among constituent components of the skin, and a fluorescence bleaching phenomenon of a fluorescent material may occur over time. In this case, the fluorescence may constitute the background in the Raman spectrum. Referring to FIG. 4, it can be seen that a point where fluorescence is generated in the Raman spectrum of each of the user A and the user B and a bleaching range are shown differently from each other depending on the skin constituent component of the user.

For example, the Raman spectrum analyzer 230 may extract the fluorescence bleaching range in which a CCD count or an intensity is reduced although the type of the Raman spectrum is the same before and after exposure for several seconds to several minutes, as the user characteristic information.

As an example, referring to view (A) of FIG. 4, when the light source 210 irradiates skin of the user A with a single light, the Raman spectrum acquirer 220 may acquire the Raman spectrum as shown in view (A) of FIG. 4. The Raman spectrum analyzer 230 may extract 2,000 a.u that is a maximum value of the fluorescence bleaching range from the Raman spectrum of the user A, and analyze the fluorescence bleaching range as the characteristic information of the user A. Similarly, the Raman spectrum analyzer 230 may extract 400 a.u that is a maximum value of the fluorescence bleaching range from the Raman spectrum of the user B shown in view (B) of FIG. 4, and analyze the fluorescence bleaching range as the characteristic information of the user B.

Referring to FIG. 4, because the fluorescence bleaching range for each of the user A and the user B may be unique to each user, the fluorescence bleaching range may be used as unique characteristic information for each user.

According to another exemplary embodiment, the Raman spectrum analyzer 230 may extract either one or both of a principal component composition ratio of the user's skin and feature information of a first principal component from the extracted fluorescence bleaching range. For example, the Raman spectrum analyzer 230 may extract the principal component composition ratio of the user's skin from the fluorescence bleaching range using a principal component analysis method. At this point, the feature information of the first principal component may be feature information about a principal component that occupies the largest proportion of the principal component composition ratio. For example, the Raman spectrum analyzer 230 may extract a principal component such as protein from the fluorescence bleaching range over time, and this may be expressed as the graph of FIG. 5.

Figure 5:
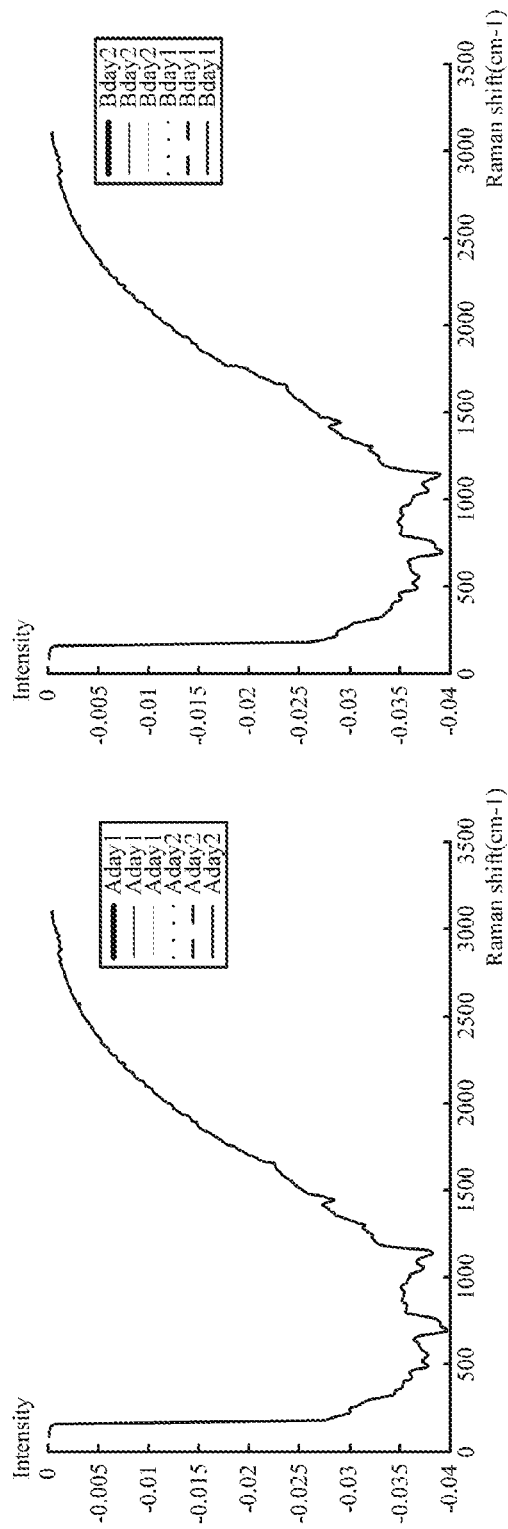
FIG. 5 is a diagram illustrating a graph related to feature information of a first principal component for each user, according to an exemplary embodiment.

FIG. 5 is a diagram illustrating a graph related to feature information of a first principal component for each user, according to an exemplary embodiment. Referring to view (A) of FIG. 5, although the Raman spectrum analyzer 230 has extracted feature information of a first principal component three times on each of a first day and a second day with respect to the user A, it can be seen that similar graphs for the user A are obtained regardless of the number of times of measurement and a measurement time (however, a minute change in the feature information of the first principal component may be generated depending on the number of times of measurement for the same user, an exposure time to a single light, and a change in the measurement time, but it is noted as a function of unique characteristic information for identifying a user). At this point, the number of times of measurement and a measurement time interval may correspond to an arbitrary number, and are not to be interpreted as being limited to the above exemplary embodiments.

The Raman spectrum analyzer 230 may extract one or more pieces of data from an outline of the graph, a Raman shift of a peak point, and an intensity of peak point as the feature information of the first principal component. That is, the Raman spectrum analyzer 230 may repeatedly measure the feature information of the first principal component at an arbitrary time and verify reproducibility of the feature information of the first principal component from the measured data.

Similarly, the Raman spectrum analyzer 230 may measure the first principal component three times on a first day (B day1) and three times on a second day (B day2) with respect to the user B and extract feature information of the first principal component of the user B as shown in view (B) of FIG. 5.

The feature information of the first principal component for each of the user A and the user B extracted by the Raman spectrum analyzer 230 may be uniquely exhibited regardless of the number of times of measurement and the measurement time for each user, and therefore may be used as the user characteristic information.

Figure 6:
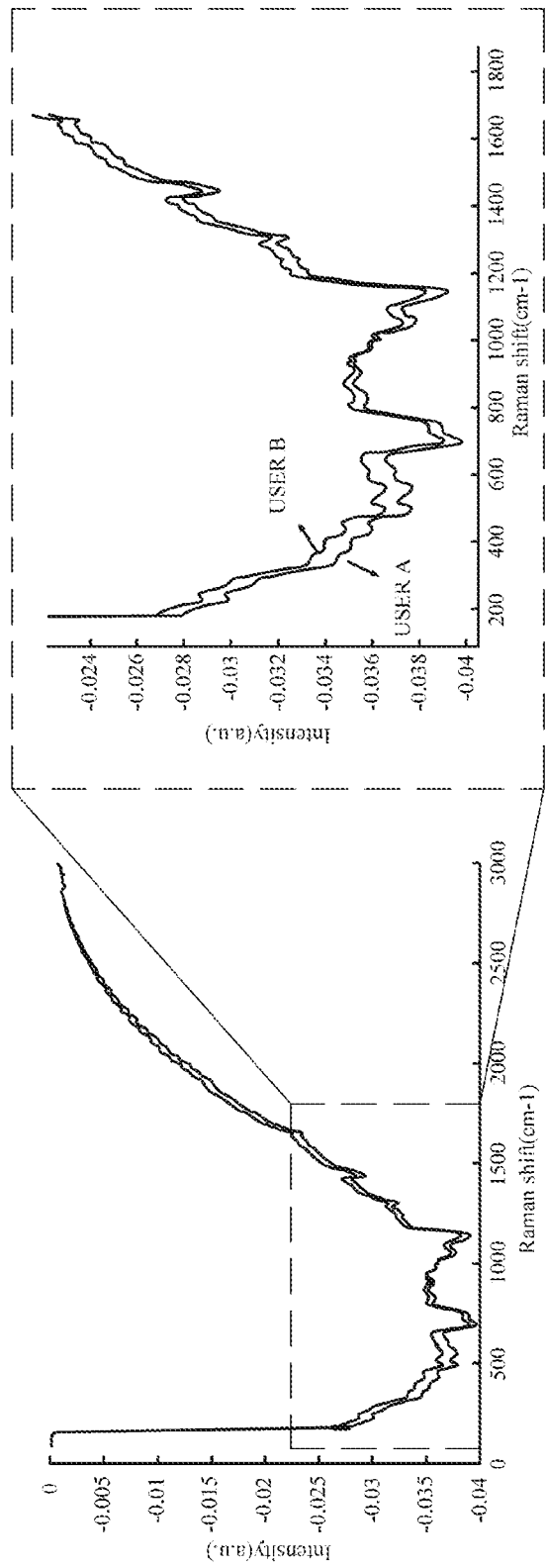
FIG. 6 is a diagram comparing graphs related to feature information of a first principal component of a user A and a user B, according to an exemplary embodiment.

FIG. 6 is a diagram comparing graphs related to feature information of a first principal component of the user A and the user B, according to an exemplary embodiment. When graphs related to the feature information of the first principal component for each user of FIG. 5 are superimposed on one another, the outline of the graph may be obtained as shown in FIG. 6. When the obtained graph is enlarged in a Raman shift region ($cm^{-1}$) of 1 to 1,800, the outline of the graph for the feature information of the first principal component of each of the user A and the user B appears different. This may be because a component composition ratio constituting the skin is different for each person, which can be confirmed by the graph shown in FIG. 6.

The Raman spectrum analyzer 230 may extract the outline of the graph, a Raman shift of the peak point, and an intensity of the peak point from the feature information of the first principal component of each of the user A and the user B, and may analyze the extracted data as the user characteristic information. In an exemplary embodiment of FIG. 6, the authenticator 240 may determine that the user A and the user B are not the same person based on the analysis result of the Raman spectrum analyzer 230.

The storage 250 may store the analysis result of the Raman spectrum analyzer 230 as unique characteristic information of a user. For example, when the Raman spectrum analyzer 230 measures the Raman spectrum six times with respect to the same user and analyzes user characteristic information from the measured Raman spectrum, the storage 250 may store a mean value of the Raman spectrum and an error range or a representative Raman spectrum and a threshold range as the user characteristic information. At this point, the storage 250 may store the Raman spectrum measured for each user in a database, a look-up table, or the like, and use a hardware device such as a memory, a storage, or the like.

When the composition ratio of the principal components of the body is changed due to increase and decrease of the user's body weight, changes in diet and lifestyle, and the like, the storage 250 may track and record the changing process, and store the latest Raman spectrum analysis result as the user characteristic information.

The authenticator 240 may authenticate a user based on the analysis result. At this point, the authenticator 240 may authenticate the user's identity by comparing the analysis result of the Raman spectrum analyzer 230 and the user characteristic information stored in advance.

When the user's identity is authenticated by the authenticator 240, the information provider 260 may process the analysis result of the Raman spectrum with respect to the authenticated user and provide information about the health status of the user. The information about the health status may be information that is described in association of the principal component composition ratio analyzed from the Raman spectrum and the feature information about the principal composition with the health status of the user.

The user authentication apparatus 200 using the Raman spectrum may perform a user authentication based on biometric information of the user in a non-invasive manner. In addition, the user authentication apparatus 200 using the Raman spectrum may perform the user authentication and provide the information about the health status of the user at the same time, and thereby may contribute to user convenience.

Figure 7:
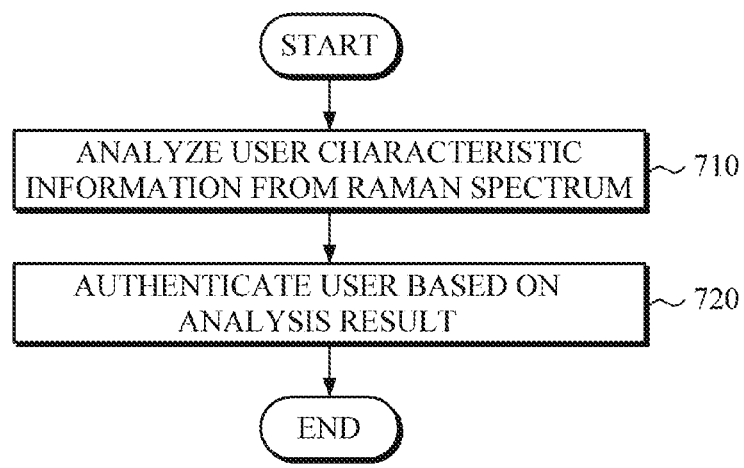
FIG. 7 is a flowchart illustrating a user authentication method using the user authentication apparatus of FIG. 1.

FIG. 7 is a flowchart illustrating a user authentication method using the user authentication apparatus of FIG. 1. As an example, a user authentication method using the user authentication apparatus 100 according to an exemplary embodiment of FIG. 1 may include the following operations.

First, in operation 710, the Raman spectrum analyzer 110 analyzes user characteristic information from a Raman spectrum. According to an exemplary embodiment, the Raman spectrum analyzer 110 may extract one or more pieces of data from a type of the Raman spectrum, a Raman shift of a peak point, and an intensity of the peak point and analyze the extracted data as user characteristic information.

Next, in operation 720, the authenticator 120 authenticates a user based on the analysis result of the Raman spectrum analyzer 110. For example, the authenticator 240 may determine whether the extracted data coincides with user characteristic information stored in advance based on the analysis result and authenticate a user's identity using the user authentication apparatus 100.

Figure 8:
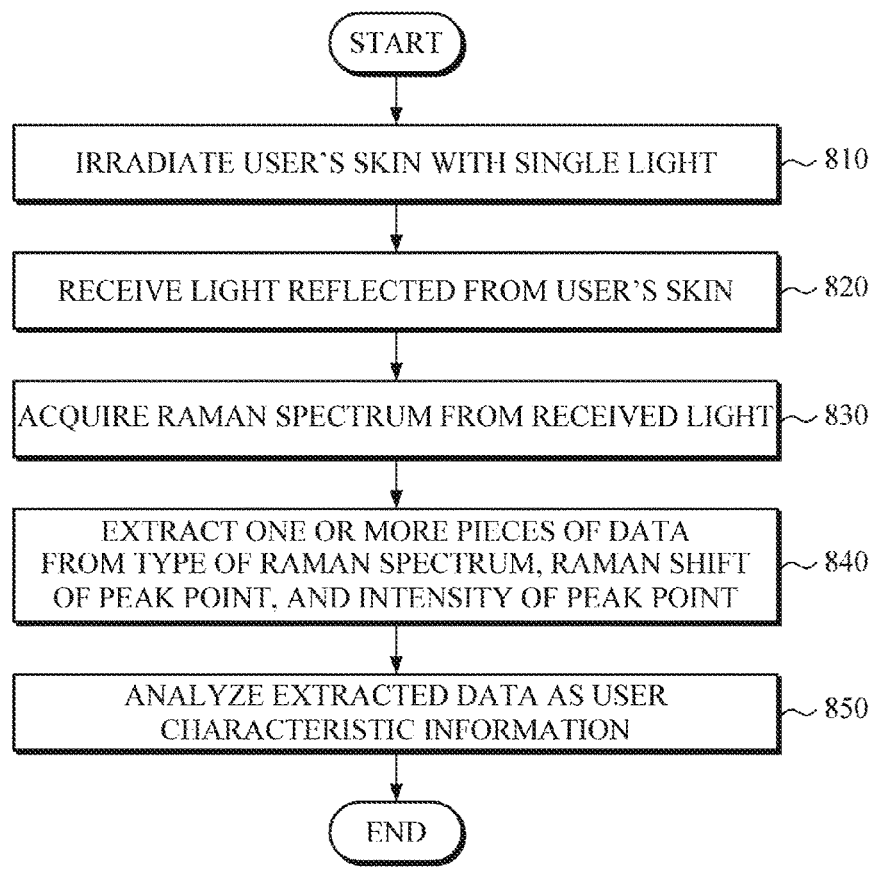
FIG. 8 is a flowchart illustrating a user authentication method using the user authentication apparatus of FIG. 2.

FIG. 8 is a flowchart illustrating a user authentication method using the user authentication apparatus 200 of FIG. 2.

First, in operation 810, the light source 210 irradiates a user's skin with a single light. In this case, the single light may be a short wavelength light such as a laser.

Next, the Raman spectrum acquirer 220 receives light reflected from the user's skin in operation 820, and acquires a Raman spectrum from the received light in operation 830. At this point, as Raman light selectively emits only multiple signals with a wavelength from a narrow wavelength band as inelastic scattering light, it is easy to discern biometric signals as compared to other methods. As an example, a wealth of molecular vibration structure information may be contained in the Raman spectrum, and the information may be used as unique characteristic information for each user. For example, depending on constituent components of a body such as blood sugar, cholesterol, collagen, keratin, etc., and a skin protein component for each user, a different type of Raman spectrum may be exhibited.

Next, in operation 840, the Raman spectrum analyzer 230 extracts one or more pieces of data from a type of the Raman spectrum, a Raman shift of a peak point, and an intensity of the peak point. As an example, the Raman spectrum analyzer 230 may repeatedly measure the Raman spectrum with respect to a user, determine a mean value of the measured Raman spectrum or a representative Raman spectrum, and extract user characteristic information from the determined Raman spectrum.

In addition, the Raman spectrum analyzer 230 may extract peak points, lowest points, the number of the peak points, the number of the lowest points, the intensity of the peak points, variation in the intensity, a mean value of the intensity within a range of a wave number, a deviation from the peak point, and other feature points from each of the Raman spectrums, and may analyze the extracted data as the user characteristic information.

Moreover, in operation 850, the Raman spectrum analyzer 230 analyzes the extracted data as the user characteristic information using a graph outline analysis method using an image processing technique, a statistical data extraction method, and a quantitative or qualitative analysis method of the Raman spectrum.

When the user characteristic information is analyzed by the Raman spectrum analyzer 230, the authenticator 240 may authenticate a user based on the analysis result. As an example, the authenticator 240 may authenticate a user's identity by comparing the analysis result and the user characteristic information stored in advance.

Figure 9:
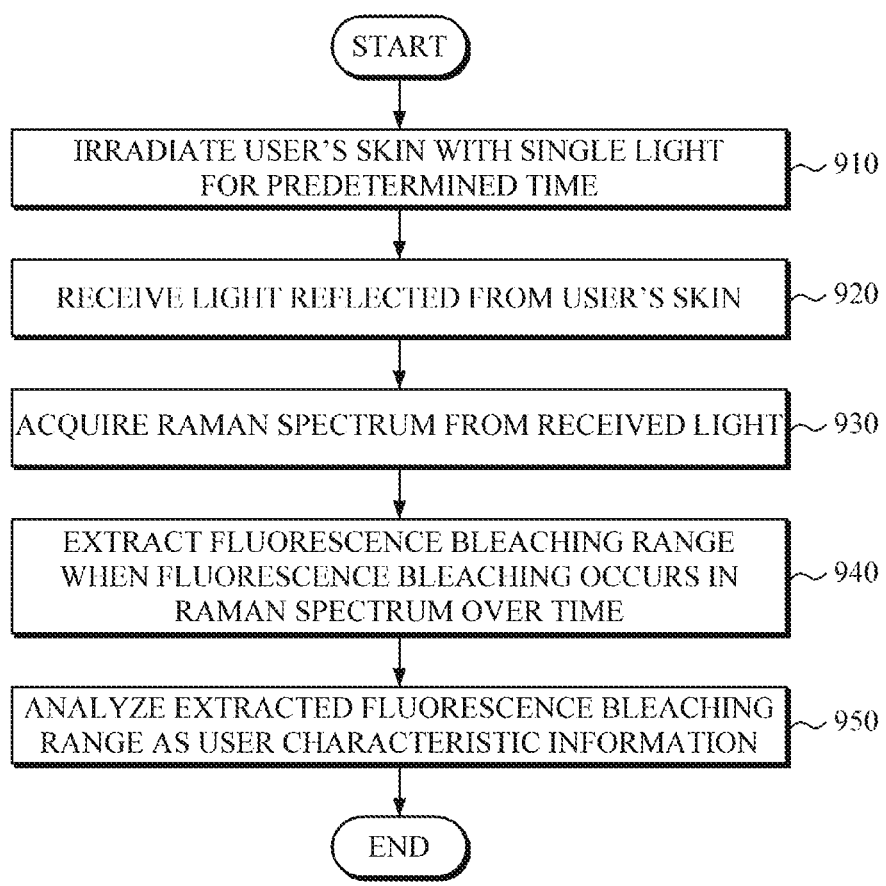
FIG. 9 is a flowchart illustrating a user authentication method according to another exemplary embodiment, using the user authentication apparatus of FIG. 2.

FIG. 9 is a flowchart illustrating a user authentication method according to another exemplary embodiment, using the user authentication apparatus 200 of FIG. 2.

Referring to FIGS. 2 and 9, in operation 910, the light source 210 irradiates the user's skin with single light for a predetermined time. Next, the Raman spectrum acquirer 220 receives light reflected from the user's skin in operation 920, and acquires the Raman spectrum that is exposed to light for a predetermined time from the received light in operation 930.

Next, in operation 940, when fluorescence bleaching occurs in the Raman spectrum over time, the Raman spectrum analyzer 230 extracts a fluorescence bleaching range. In operation 950, the Raman spectrum analyzer 230 analyzes the extracted fluorescence bleaching range as the user characteristic information. As an example, a point where fluorescence is generated in the Raman spectrum of each of the user A and the user B and a bleaching range may be shown differently from each other depending on the skin constituent component of the user. Because the fluorescence bleaching range for each of the user A and the user B may be unique to each user, the fluorescence bleaching range may be used as unique characteristic information for each user.

For example, the Raman spectrum analyzer 230 may extract the fluorescence bleaching range in which a CCD count or intensity is reduced although the type of the Raman spectrum is the same before and after exposure for several seconds to several minutes, as the user characteristic information.

Figure 10:
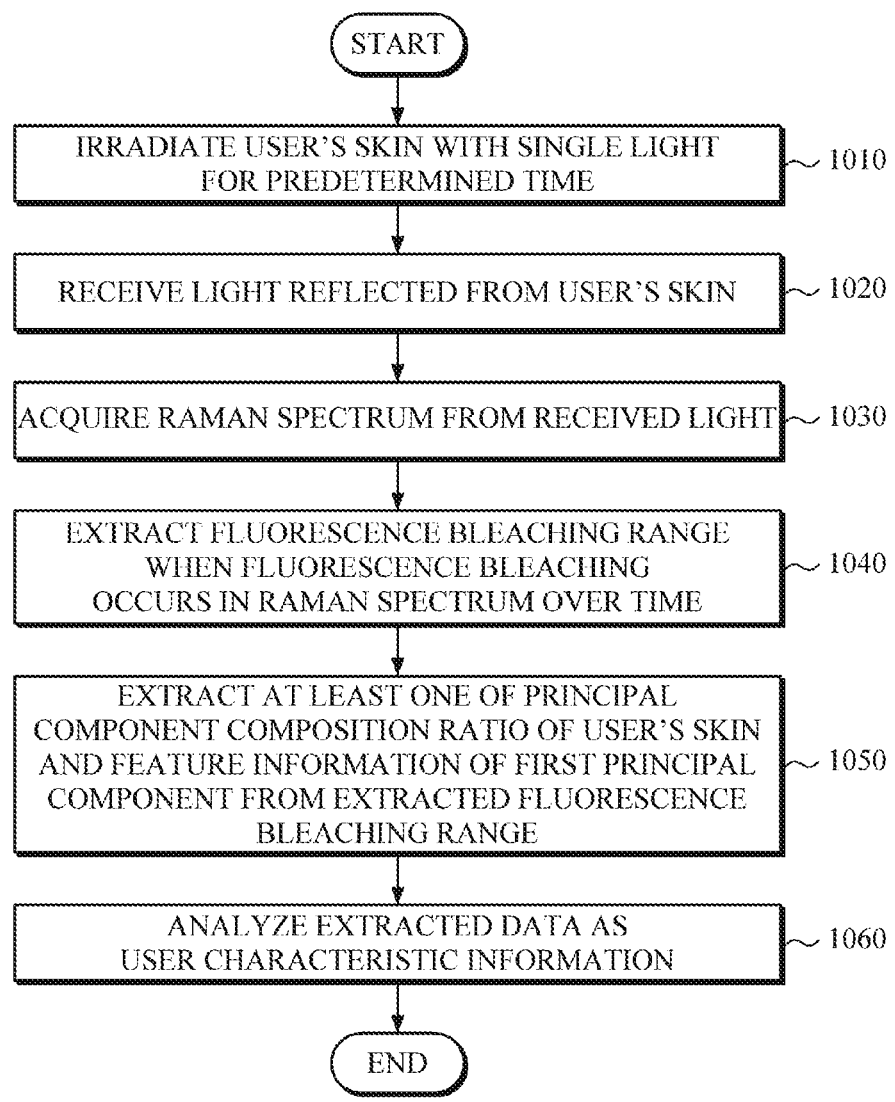
FIG. 10 is a flowchart illustrating a user authentication method according to yet another exemplary embodiment, using the user authentication apparatus of FIG. 2.

FIG. 10 is a flowchart illustrating a user authentication method according to still another exemplary embodiment, using the user authentication apparatus 200 of FIG. 2. Referring to FIGS. 2 and 10, in operation 1010, the light source 210 irradiates the user's skin with single light for a predetermined time. Next, the Raman spectrum acquirer 220 receives light reflected from the user's skin in operation 1020, and acquires a Raman spectrum from the received light in operation 1030.

Next, in operation 1040, when fluorescence bleaching occurs in the Raman spectrum over time, the Raman spectrum analyzer 230 extracts a fluorescence bleaching range.

Next, in operation 1050, the Raman spectrum analyzer 230 extracts at least one of a principal component composition ratio of the user's skin and feature information of a first principal component from the extracted fluorescence bleaching range. The Raman spectrum analyzer 230 may extract the principal component composition ratio of the user's skin from the fluorescence bleaching range using a principal component analysis method. At this point, the feature information of the first principal component may be feature information about a principal component that occupies the largest proportion of the principal component composition ratio.

As an example, the Raman spectrum analyzer 230 may extract a principal component such as protein from the fluorescence bleaching range over time, and extract feature information of a first principal component. In operation 1060, when the feature information of the first principal component is shown as a graph, the Raman spectrum analyzer 230 may extract one or more pieces of data from the outline of the graph, a Raman shift of a peak point, and an intensity of the peak point, and analyzes the extracted data as user characteristic information.

In addition, the Raman spectrum analyzer 230 may repeatedly measure feature information of the first principal component at arbitrary time, and verify the reproducibility of the feature information of the first principal component from the measured data. At this point, the number of times of measurement and the measurement time interval may correspond to an arbitrary number, and are not to be interpreted as being limited to the above exemplary embodiments.

The feature information of the first principal component extracted by the Raman spectrum analyzer 230 may be uniquely exhibited regardless of the number of times of measurement and the measurement time for each user, and therefore may be used as the user characteristic information.

In addition, the storage 250 may store the analysis result of the Raman spectrum analyzer 230 as unique characteristic information of a user. For example, when the Raman spectrum analyzer 230 measures the Raman spectrum six times with respect to the same user and analyzes user characteristic information from the measured Raman spectrum, the storage 250 may store a mean value of the Raman spectrum and an error range or the representative Raman spectrum and a threshold range as the user characteristic information.

When the composition ratio of the principal components of the body is changed due to increase and decrease of the user's body weight, changes in diet and lifestyle, and the like, the storage 250 may track and record the changing process, and store the latest Raman spectrum analysis result as the user characteristic information.

The authenticator 240 may authenticate a user based on the analysis result. At this point, the authenticator 240 may authenticate the user's identity by comparing the analysis result of the Raman spectrum analyzer 230 and user characteristic information stored in advance.

When the user's identity is authenticated by the authenticator 240, the information provider 260 may process the analysis result of the Raman spectrum with respect to the authenticated user and provide information about the health status of the user. The information about the health status may be information that is described in association of the principal component composition ratio analyzed from the Raman spectrum and the feature information about the principal composition with the health status of the user.

The user authentication apparatus 200 using the Raman spectrum may perform a user authentication based on biometric information of the user in a non-invasive manner. In addition, the user authentication apparatus 200 using the Raman spectrum may perform the user authentication and provide the information about the health status of the user at the same time, and thereby may contribute to user convenience.

The functions of the apparatus and method disclosed in this application may be realized as computer-readable codes in computer-readable recording media. The computer-readable recording media include all kinds of recording devices in which data that is readable by a computer system is stored.

The computer-readable recording media include all kinds of recording devices in which data that are readable by a computer system are being stored. Examples of the computer-readable recording media include a read-only memory (ROM), a random access memory (RAM), a compact-disc ROM (CD-ROM), a magnetic tape, a floppy disk, an optical data storage device, etc., and may be also realized in the form of a carrier wave (for example, transmission through the Internet). In addition, the computer-readable recording media may be distributed into the computer system that is connected through the networks to store and implement the computer-readable codes in a distribution mechanism. Furthermore, functional programs, codes and code segments, all of which are used to practice exemplary embodiments, may be easily deduced by programmers in the art to which the exemplary embodiments belong.

A number of examples have been described above. Nevertheless, it may be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A user authentication apparatus using a Raman spectrum, the user authentication apparatus comprising:
   a light source configured to irradiate light to skin of a user, for a predetermined time; and
   a Raman spectrum acquirer configured to:
      receive that is reflected from the skin; and
      acquire the Raman spectrum of the user, from the light that is received;
   a Raman spectrum analyzer configured to analyze, in response to fluorescence bleaching occurring in the Raman spectrum over time:
      extract a fluorescence bleaching range from the Raman spectrum; and
      analyze the fluorescence bleaching range that is extracted, as user characteristic information; and
   an authenticator configured to authenticate the user, based on the user characteristic information that is analyzed.

2. The user authentication apparatus of claim 1, wherein the Raman spectrum analyzer is further configured to:
   extract, from the Raman spectrum, data comprising any one or any combination of a type of the Raman spectrum, a Raman shift of a peak point, and an intensity of the peak point; and
   analyze the data that is extracted, as the user characteristic information.

3. The user authentication apparatus of claim 1, wherein the Raman spectrum analyzer is further configured to:
   extract, from the fluorescence bleaching range that is extracted, data comprising either one or both of a principal component composition ratio of the skin of the user and feature information of a first principal component; and
   analyze the data that is extracted, as the user characteristic information.

4. The user authentication apparatus of claim 3, wherein the Raman spectrum analyzer is further configured to extract, from the fluorescence bleaching range that is extracted, the principal component composition ratio of the skin of the user, using a principal component analysis method.

5. The user authentication apparatus of claim 3, wherein the feature information of the first principal component occupies a largest proportion of the principal component composition ratio.

6. The user authentication apparatus of claim 3, wherein the Raman spectrum analyzer is further configured to:
   repeatedly measure the feature information of the first principal component at an arbitrary time; and
   verify reproducibility of the feature information that is measured.

7. The user authentication apparatus of claim 1, further comprising:
   a storage configured to store the user characteristic information that is analyzed,
   wherein the authenticator is further configured to authenticate an identify of the user by comparing the user characteristic information that is analyzed and pre-stored user characteristic information.

8. The user authentication apparatus of claim 1, further comprising:
   an information provider configured to:
      process the user characteristic information that is analyzed, with respect to the user that is authenticated; and
      provide information of a health status of the user that is authenticated.

9. A user authentication method using a Raman spectrum, the user authentication method comprising:
   irradiating light to skin of a user, for a predetermined time;
   receiving light that is reflected from the skin;
   acquiring the Raman spectrum of the user, from the light that is received;
   in response to fluorescence bleaching occurring in the Raman spectrum over time:
      extracting a fluorescence bleaching range from the Raman spectrum; and
      analyzing the fluorescence bleaching range that is extracted, as user characteristic information; and
   authenticating the user, based on the user characteristic information that is analyzed.

10. The user authentication method of claim 9, further comprising:
    extracting, from the Raman spectrum, data comprising any one or any combination of a type of the Raman spectrum, a Raman shift of a peak point, and an intensity of the peak point; and
    analyzing the data that is extracted, as the user characteristic information.

11. The user authentication method of claim 9, wherein the analyzing the fluorescence bleaching range comprises:
    extracting, from the fluorescence bleaching range that is extracted, data comprising either one or both of a principal component composition ratio of the skin of the user and feature information of a first principal component; and
    analyzing the data that is extracted, as the user characteristic information.

12. The user authentication method of claim 11, wherein the analyzing the fluorescence bleaching range further comprises extracting, from the fluorescence bleaching range that is extracted, the principal component composition ratio of the skin of the user, using a principal component analysis method.

13. The user authentication method of claim 11, wherein the feature information of the first principal component occupies a largest proportion of the principal component composition ratio.

14. The user authentication method of claim 11, wherein the analyzing the fluorescence bleaching range further comprises:
    repeatedly measuring the feature information of the first principal component at an arbitrary time; and verifying reproducibility of the feature information that is measured.

15. The user authentication method of claim 9, further comprising:
   storing the user characteristic information that is analyzed,
   wherein the authenticating the user comprises authenticating an identify of the user by comparing the user characteristic information that is analyzed and pre-stored user characteristic information.

16. The user authentication method of claim 9, further comprising:
   processing the user characteristic information that is analyzed, with respect to the user that is authenticated; and
   providing information of a health status of the, user that is authenticated.

* * * * *